(12) United States Patent
Malinda et al.

(10) Patent No.: US 6,309,818 B1
(45) Date of Patent: Oct. 30, 2001

(54) SCRATCH WOUND ASSAY DEVICE

(75) Inventors: Katherine M. Malinda, Millersville, MD (US); Alan O. Kusakabe, Brooklyn, NY (US); Annette B. Wysocki, Bethesda; James V. Sullivan, Bowie, both of MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 09/496,134

(22) Filed: Feb. 1, 2000

(51) Int. Cl.[7] .......................................... C12Q 1/00
(52) U.S. Cl. ........................ 435/4; 435/309.1; 600/570; 600/306
(58) Field of Search ............................. 435/309.1, 309.4, 435/4; 600/306, 562, 564, 569, 570

(56) References Cited

U.S. PATENT DOCUMENTS

| | | | |
|---|---|---|---|
| 3,597,326 | * | 8/1971 | Liner . |
| 4,012,288 | * | 3/1977 | Lyman et al. . |
| 4,599,315 | * | 7/1986 | Terasaki et al. ...................... 435/301 |
| 5,011,779 | * | 4/1991 | Maimon . |

* cited by examiner

Primary Examiner—David A. Redding
(74) Attorney, Agent, or Firm—Fish & Richardson, P.C.

(57) ABSTRACT

An apparatus having at least one template opening for causing a substantially reproducible injury to a cell, organ or tissue layer. The apparatus is useful in determining the effects of cell growth and migration agents in model wounds produced in the cell, organ or tissue layer. Also provided are methods of using the apparatus including juxtapositioning the apparatus to cells on a cell growth substrate and disrupting cells thereon.

21 Claims, 4 Drawing Sheets

SCRATCH WOUND ASSAY DEVICE

STATEMENT AS TO FEDERALLY SPONSORED RESEARCH

This invention was made in part with funds from the National Institutes of Health, Intramural Program. The government may have certain rights in this invention.

TECHNICAL FIELD OF THE INVENTION

The invention relates generally to a tissue culture apparatus and methods of inducing a substantially reproducible wounding of cell, organ or tissue cultures for scratch wound assays.

BACKGROUND OF THE INVENTION

Conventional multiple well tissue culture plates as taught by Liner (U.S. Pat. No. 3,597,326) and Lyman (U.S. Pat. No. 4,012,288) are a common tool in most tissue culture experiments requiring small numbers of cells in relatively small volumes under multiple experimental conditions. The Terisaki tissue culture plate (U.S. Pat. No. 4,599,315) is used mainly in experiments aimed at cloning cells. Among the advantages of multiple well tissue culture plates are their low cost, disposable nature, and multiplicity of cell culture compartments. Multiple well tissue culture plates make possible multiple separate cultures all within a single culture device, thus making them attractive in screening assays. Multiple well tissue culture plates are available in standard configurations (e.g., 6, 12, 24, 48 or 96 wells per plate) which allow users to select a plate which has the desired well volume most suitable for a specific application. Plates with many wells, such as 48 or 96 well plates, are a good tool for use in experiments with many variables or experiments with a small number of cells. Plates with fewer numbers of wells that are larger in size are typically used in lieu of numerous separate cell culture flasks. It is the ability to handle a complete cell culture experiment with multiple parameters in an individual plate that makes these devices a common tool in most tissue culture experiments.

Previous studies have used a "scratch" wound closure assay to assess the potential effects of an agent on in vitro cell migration. However, presently available techniques result in non-reproducible model wounds which create difficulties in assessing the reproducibility of cellular migration and the dynamic process of wound repair.

SUMMARY OF THE INVENTION

The invention provides useful techniques, devices and systems for providing a substantially reproducible model wound in a tissue culture system to assess wound repair and cell migration.

The invention provides an apparatus having at least one template opening for causing a substantially reproducible injury to a cell, organ or tissue layer. The apparatus is useful in determining the effects of cell growth and migration agents in modeling wound closure produced in the cell, organ or tissue layer. The apparatus is useful in determining the effects of chemical, biochemical, biologic or bioengineered agents on cell growth and migration of any cell type. Also provided are methods of using the apparatus including juxtapositioning the apparatus to cells on a cell growth substrate and disrupting cells exposed through the template openings.

In one embodiment, a method of disrupting cells, comprising positioning in proximity a device including a template opening with a cell growth substrate having thereon a cell, organ or tissue layer; and exposing the cell, organ or tissue layer to a disruption medium through the template opening, wherein the disruption medium contacts the cells of the cell, organ or tissue layer; and disrupting the cells by contacting the cells with the disruption medium. The disruption medium can be any medium that is capable of causing injury to a cell, organ or tissue layer including photobleaching, laser ablation, UV exposure, thermal ablation, and mechanical disruption.

The cell culture growth substrate can be a multi-well tissue culture plate, a slide or planar surface. The template opening may be square, round, oblong or rectangular, but is typically longer than it is wide. In one embodiment the template opening is about 1.0 mm to about 2.0 mm wide and about 5 mm to about 9 mm in length.

In another embodiment, the invention provides an apparatus for use with a disruption medium for disrupting cells, the apparatus comprising a template opening to guide the disruption medium (e.g., a scratch device) and thereby limit disruption of the cells. The apparatus may contain at least one well, the well having at least one wall, a top and a bottom spaced apart from the top thereby defining a volume and having located therein the template opening.

In yet another embodiment, the invention provides an apparatus for guiding a scratch device during disruption of a cell, organ or tissue layer, the apparatus comprising a template opening sized to receive the scratch device and guide a tip thereof protruding from said template opening during disruption of a juxtaposed cell, organ or tissue layer.

In another embodiment, the invention provides a tray, comprising at least one well having an opening at the top and bottom and defining a first predetermined volume, and a template opening defining the bottom of the well, wherein a disruption medium may be directed through the template opening. The tray can be designed to be adaptably coupled to a reservoir, the reservoir defining a second predetermined volume greater than the first predetermined volume.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
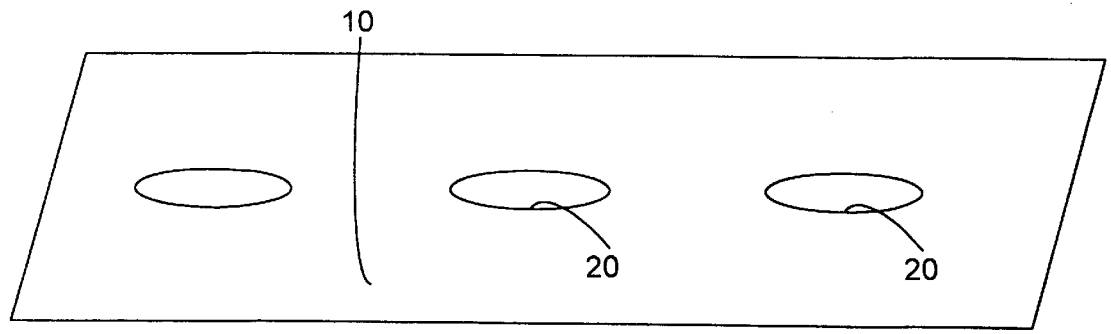
FIG. 1 is a schematic drawing of a scratch device tray, scratch stick device and cell culture substrate.
Figure 1:
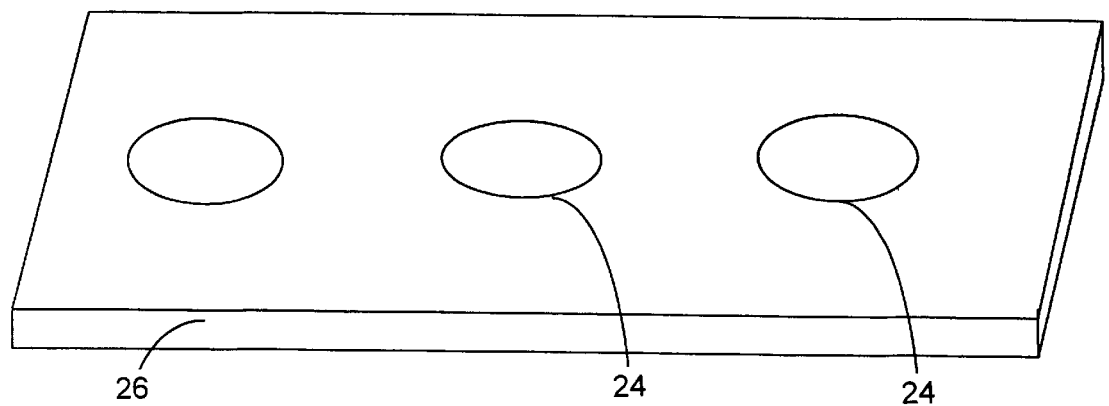
Figure 1:
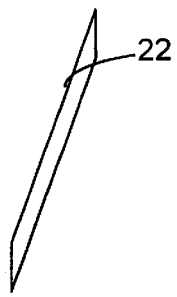

Wounds in tissues undergo a complex and ordered series of events to repair the tissue. The series of events may include infiltration of inflammatory immune cells as part of the process to remove and destroy necrotic tissue, increased vascularization by angiogenic factors and increased cell proliferation and extracellular matrix deposition. Although the basic process of tissue repair has been characterized, the individual steps and factors necessary to carry out this complex series of events are not well understood. The identification of individual steps and factors could lead to improved methods for the treatment of diseases resulting from inadequate wound repair processes.

There is currently a desire to develop a way of reproducibly injuring a layer of cells to study the effects of different compounds or treatments on the ability of the remaining cells to repair the damaged area. Provided is a device that reproducibly makes a wound of a desired size (e.g., 1.5 mm wide) in a cell layer grown on a cell culture material (e.g., an 8 well slide). Accordingly, the invention provides researchers with a faster, more accurate way of screening large numbers of factors.

By "cell growth substrate" means any number of materials and compositions, many of which are currently commercially available, including for example, a tissue culture plate of a rectangular or circular shape having a growth area of about 1 $cm^2$ to greater than 200 $cm^2$, multiwell tissue culture plates having 2 wells to more than 90 wells per tissue culture plate, and tissue specimen slides as used in microscopic analysis. Other cell growth surfaces and devices are readily apparent to those of skill in the art. The apparatus of the invention can be used with any of the foregoing cell or tissue culture plates, slides and devices.

In one embodiment, the invention provides a method for creating a substantially reproducible disruption of a cell, organ or tissue layer, comprising juxtapositioning a tray, comprising at least one template each defining an opening and configured so that each template can be juxtaposed to a corresponding cell culture growth substrate. Each cell culture growth substrate can be disrupted by a disruption medium (e.g., a scratch stick device) exposed through each template opening, wherein the disruption medium contacts the cells of the cell, organ or tissue layer. The cells are disrupted by contacting the cells with the disruption medium (e.g., forcibly contacting the cell with a scratch stick device). This method is extremely useful to the cosmetics and pharmaceutical companies in assessing the affect of an agent on cell migration and repair to a damaged cell layer.

Depending on the cell type used, one could use the device of the invention as a high throughput screening device for testing products such as blood vessel promoting or inhibiting compounds and for studying the effects of compounds on migration and proliferation of different cell types (for toxicology studies). This later test is important to cosmetic and drug companies since many current tests are done using animals. The invention allows for toxicology and irritancy studies to be rapidly carried out on a variety of cell types potentially limiting the need for animal studies.

With reference to FIG. 1, the invention provides a tray 10 having a plurality of template openings 20. Each template opening 20 is of a size sufficient for causing disruption of a cell, tissue or organ layer by contacting the cells with a disruption medium. For example, in one embodiment the opening is of sufficient size for inserting a scratch stick device 22. The tray 10 is designed to be juxtaposed or placed in proximity to cells 24 on a cell growth substrate 26.

By "juxtaposed" or "proximity" means a distance from the template opening 20 to the cell growth substrate 26 sufficient to avoid unwanted lateral movement of a scratch device 22 or diffusion or diffraction of light, depending upon the disruption medium used, during operation. Thus, the distance from the bottom of the tray 10 to the cell growth substrate 26 should be minimized to avoid lateral movement of the scratch device or diffraction of a light (UV and/or laser) source as the medium is exposed to the cell layer through a template opening 20. A typical distance is about 1 mm or less and will depend upon the size of the opening 20 and the size of the scratch stick device 22 or intensity of the light.

Accordingly, in one embodiment, during use a scratch device is inserted through the template opening 20 such that it agitates and causes disruption of the cells on the cell growth substrate.

Figure 2:
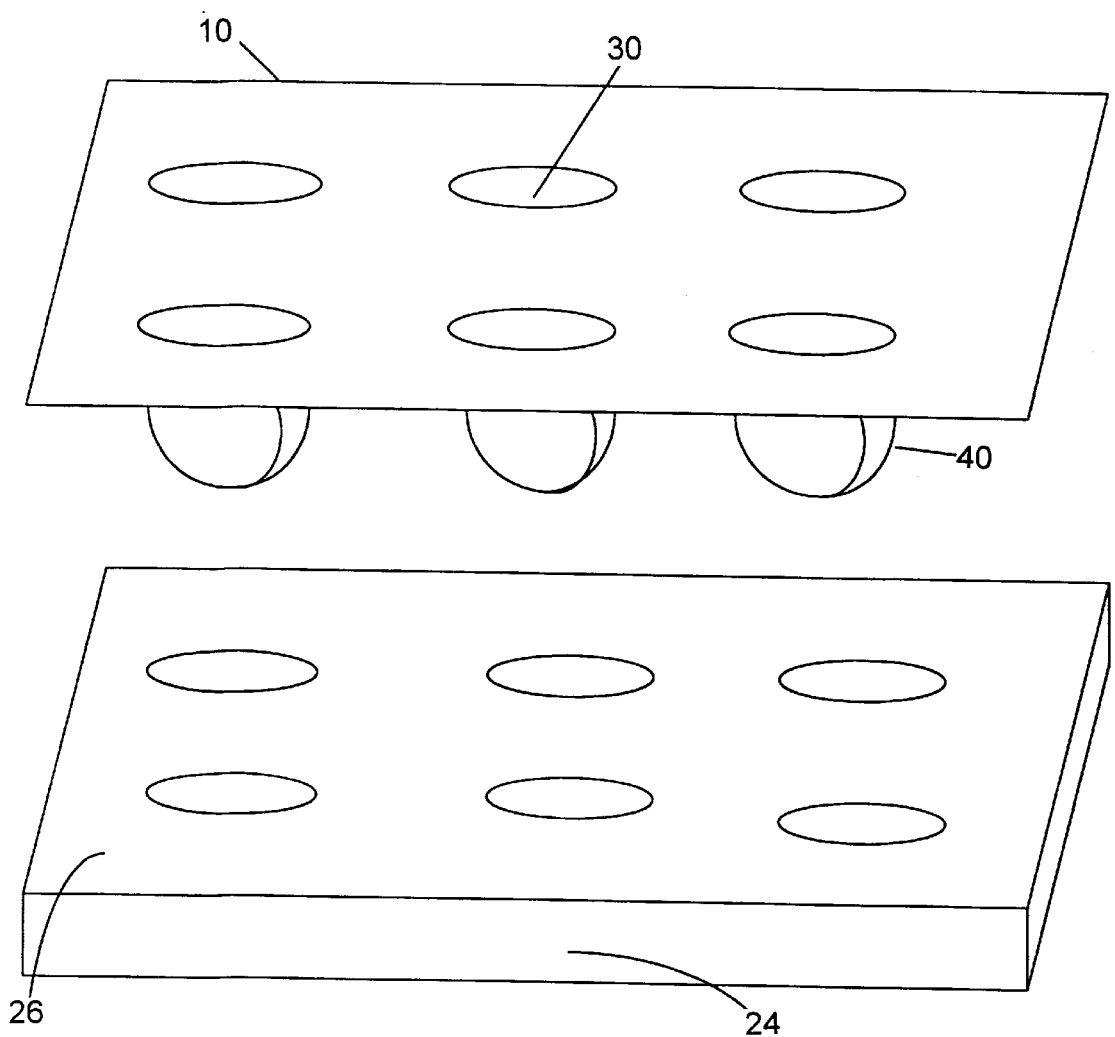
FIG. 2 is a schematic drawing of the scratch device tray demonstrating the tray's adaptability to multi-well cell culture substrates.

A tray 10 as depicted in FIG. 1 can be used with any number of cell growth devices as described above. For example, the tray 10 may be placed in juxtaposition with cells on a slide or tissue culture plate. A scratch stick device 22 is then inserted through each template opening 20 to contact the cells. The scratch stick device is then rotated or moved longitudinally in the template opening 20 in order to disrupt the cells on the cell growth substrate 26. Alternatively, the cells are exposed to a disruption medium such as, for example, light or heat.

Where the cell growth substrate 26 is a multi-well tissue culture plate, the template openings 20 can be adaptably designed to fit within the area defined by the wells of the tissue culture plate. With references to FIGS. 2 and 3, a tray 10 comprises a plurality of wells 40, each well having at least one wall and having an entrance 30 at the top of the tray. Each well 40 is adapted to fit within the volume defined by the wells of a multi-well tissue culture plate such that the bottom of the well 45 is juxtaposed or in proximity to cells growing on the bottom of the well of the multi-well tissue culture plate. Each well 40 has at least one wall defining the well. The well may be for example rectangular, orthogonal, square or circular.

Figure 3:
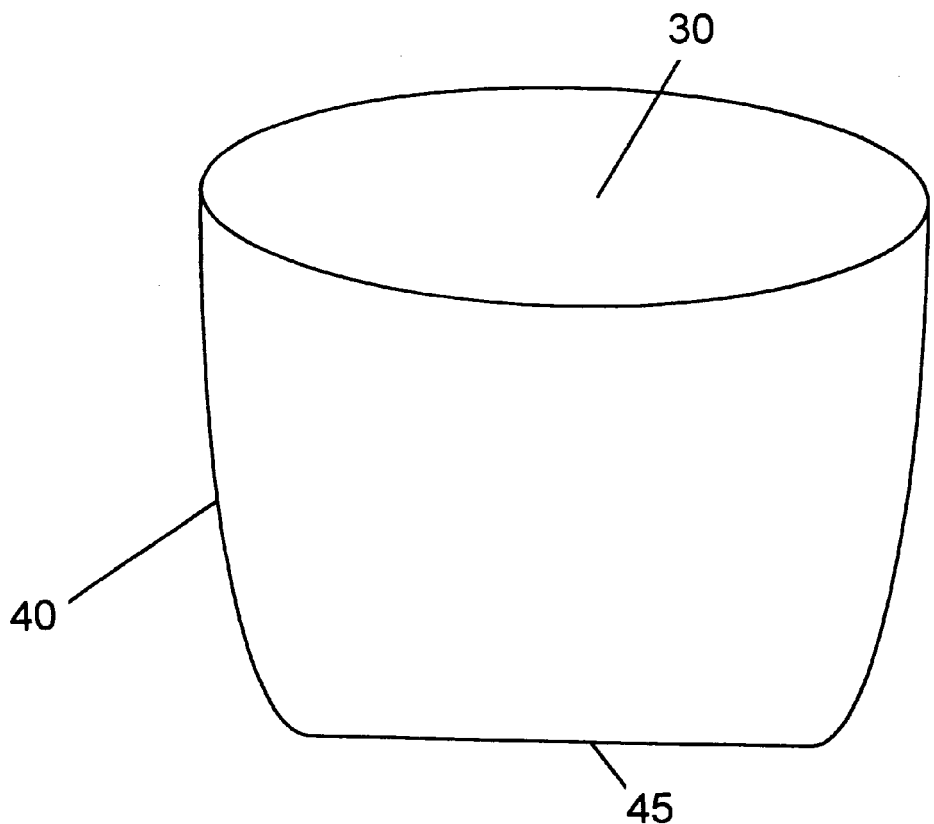
FIG. 3 is a schematic drawing of a well of the scratch device tray of FIG. 2.
Figure 4:
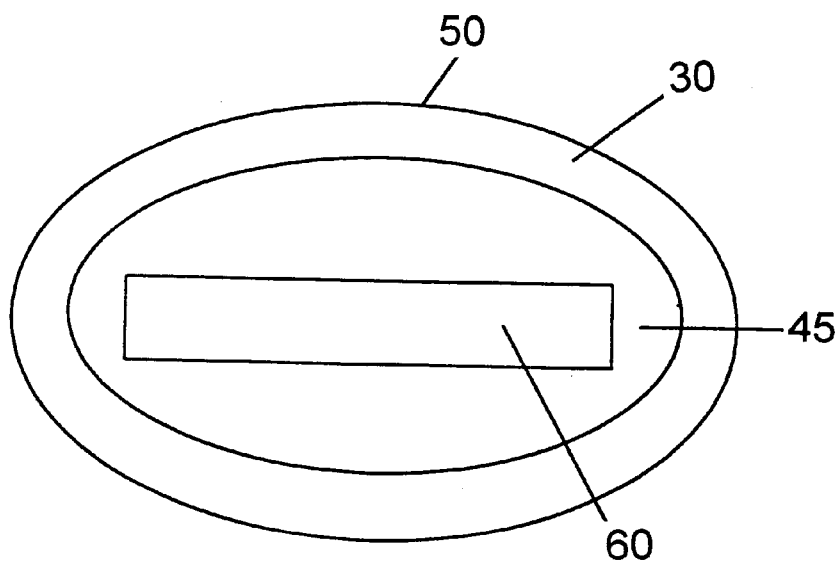
FIG. 4 is a schematic view of the well of FIG. 3 from above the well.
Figure 5:
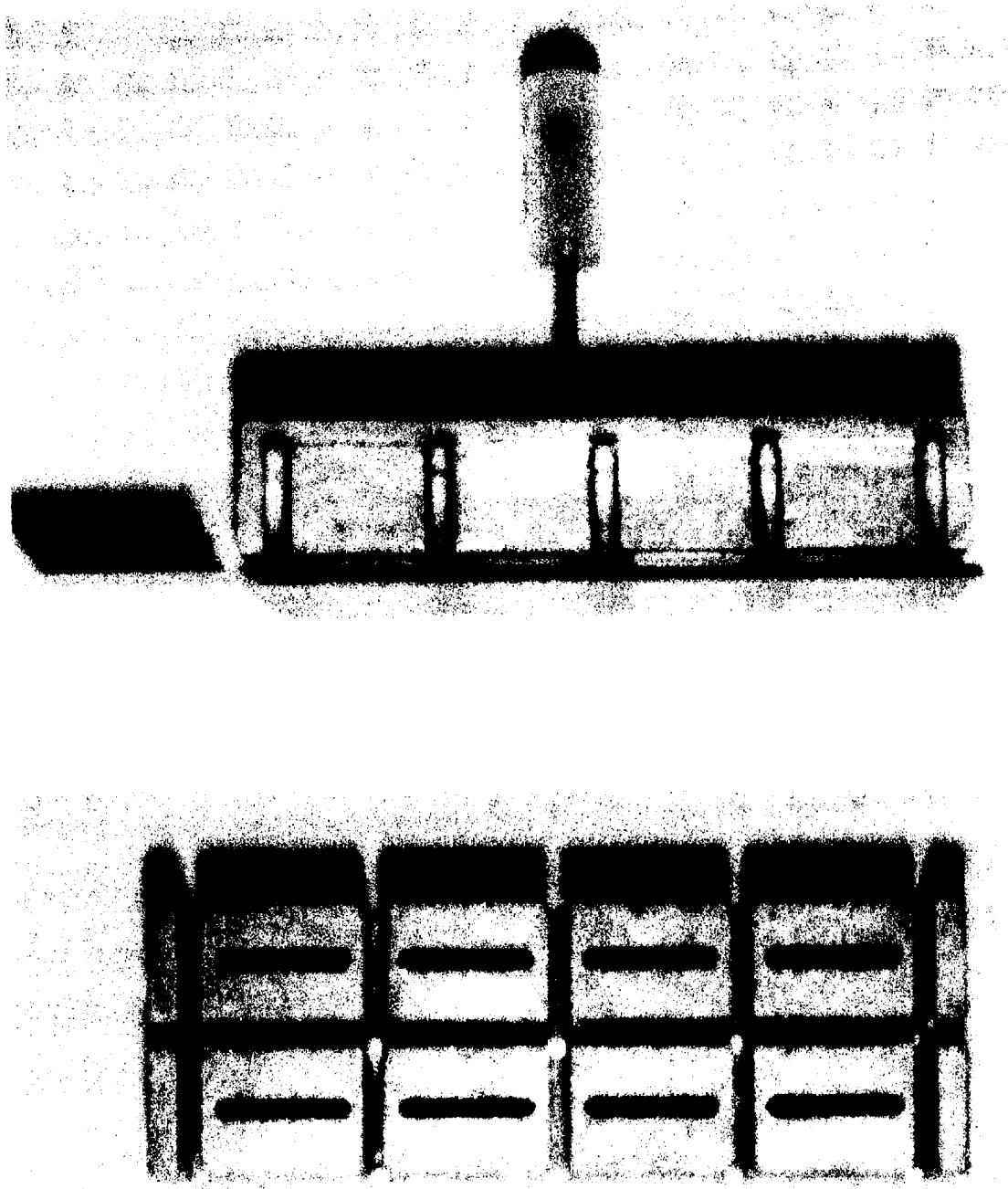
FIG. 5 is a photograph of a scratch device used with a cell culture substrate.

FIG. 4 is a top view of the well of FIG. 3. Each well 40 comprises at least one wall 50, an entrance 30, a bottom 45, and a template opening 60. During operation, the well 40 is used with a tissue growth substrate 26 such that the bottoms 45 and hence the template opening 60, are placed in juxtaposition with cells growing on the cell growth substrate 26. A disruption medium, such as a scratch stick device 22, is then exposed through each entrance 30 and guided by the corresponding template opening 60 such that the disruption medium (e.g., a scratch device 22) contacts the cells growing on the cell growth substrate 26.

A disruption medium used in the invention can be, for example, light (e.g., photobleaching, laser ablation, UV exposure), heat or mechanical injury (e.g., a scratch device). A scratch device used in the invention can be any material of sufficient size to extend through the opening of the apparatus (e.g., the template opening 60). For example, a suitable scratch stick device of the invention includes a toothpick, spatula (e.g., a weighing spatula used in laboratories), a stainless steel stick, and a razor blade.

The apparatus of the invention can be made out of any number of biocompatible materials so long as they are not toxic to cells. For example, suitable materials for the tray include biocompatible polymers (e.g., polystyrene, polypropylene), glass, stainless steel, ceramics and other materials known in the art.

A number of embodiments of the invention have been described. Nevertheless, it will be understood that various modifications may be made without departing from the spirit and scope of the invention. Accordingly, other embodiments are within the scope of the following claims.

What is claimed is:

1. A method of disrupting cells, comprising:
   positioning a device including a template opening in proximity to a cell growth substrate having cells thereon;
   exposing the cells to a disruption medium through the template opening; and
   disrupting the exposed cells by contacting such cells with the disruption medium.

2. The method of claim 1, wherein the cell culture growth substrate is a multi-well tissue culture plate.

3. The method of claim 1, wherein the cell culture growth substrate is a planar surface.

4. The method of claim 3, wherein the planar surface is a cell culture slide.

5. The method of claim 1, wherein the template opening is longer than it is wide.

6. The method of claim 5, wherein the width of the template opening is about 1.0 mm to about 2.0 mm.

7. The method of claim 6, wherein the width of the template is about 1.5 mm.

8. The method of claim 5, wherein the length of the template opening is about 5 mm to about 9 mm.

9. The method of claim 1, wherein the disruption medium is selected from the group consisting of light, heat and a scratch stick device.

10. An apparatus for use with a disruption medium for disrupting cells, the apparatus comprising a template opening to guide the disruption medium and thereby limit disruption of the cells, wherein the apparatus is designed to be placed in proximity to cells on a growth substrate.

11. The apparatus of claim 10, wherein the apparatus is a tray.

12. The apparatus of claim 11, wherein the tray further comprises a well.

13. The apparatus of claim 12, further comprising a plurality of wells, each well having at least one wall, a top and a bottom spaced apart from the top thereby defining a volume and having located therein the template opening.

14. The apparatus of claim 13, wherein each well is sized to be adaptably coupled with a cell culture growth substrate.

15. The apparatus of claim 13, wherein the bottom of each well is a fixed distance from the top of the tray.

16. The apparatus of claim 11, wherein each template opening is longer than it is wide.

17. The apparatus of claim 11, wherein the disruption medium is selected from the group consisting of light, heat and a scratch stick device.

18. An apparatus for guiding a scratch stick device during disruption of a cell, organ or tissue layer, the apparatus comprising:
   a template opening sized to receive the scratch device and guide a tip thereof protruding from said template opening during disruption of a cell, organ or tissue layer,
   wherein the apparatus is designed to be placed in proximity to cells on a growth substrate.

19. A tray, comprising:
   a) at least one well having an opening at the top and bottom and defining a first predetermined volume, and
   b) a template opening defining the bottom of the well, wherein a scratch stick device may be inserted through the template opening, wherein the tray is designed to be placed in proximity to cells on a growth substrate.

20. The tray of claim 19, wherein the tray is designed to be adaptably coupled to a plurality of reservoirs, each reservoir defining a second predetermined volume greater than the first predetermined volume.

21. The apparatus of claim 19, wherein said template opening is longer than it is wide.

* * * * *